US008491478B2

(12) United States Patent
Lee et al.

(10) Patent No.: US 8,491,478 B2
(45) Date of Patent: Jul. 23, 2013

(54) ULTRASOUND SYSTEM AND METHOD OF PROVIDING COLOR M MODE IMAGE AND BRIGHTNESS M MODE IMAGE

(75) Inventors: Kwang Ju Lee, Seoul (KR); Jong Sik Kim, Seoul (KR)

(73) Assignee: Medison Co., Ltd., Kangwon-Do (KR)

( * ) Notice: Subject to any disclaimer, the term of this patent is extended or adjusted under 35 U.S.C. 154(b) by 554 days.

(21) Appl. No.: 12/756,000

(22) Filed: Apr. 7, 2010

(65) Prior Publication Data
US 2010/0256491 A1 Oct. 7, 2010

(30) Foreign Application Priority Data

Apr. 7, 2009 (KR) .................. 10-2009-0029678

(51) Int. Cl.
*A61B 8/00* (2006.01)
(52) U.S. Cl.
USPC ........................................ 600/441
(58) Field of Classification Search
USPC ........................... 600/440, 441, 437
See application file for complete search history.

(56) References Cited

U.S. PATENT DOCUMENTS

| 4,817,617 | A | | 4/1989 | Takeuchi et al. | |
|---|---|---|---|---|---|
| 5,800,356 | A | * | 9/1998 | Criton et al. | 600/441 |
| 5,916,168 | A | * | 6/1999 | Pedersen et al. | 600/443 |
| 6,050,944 | A | * | 4/2000 | Holley et al. | 600/441 |
| 7,532,747 | B2 | * | 5/2009 | Yao et al. | 382/128 |
| 7,670,293 | B2 | * | 3/2010 | Dubberstein et al. | 600/453 |
| 2003/0045795 | A1 | | 3/2003 | Bjaerum et al. | |
| 2006/0173327 | A1 | | 8/2006 | Kim | |
| 2008/0228078 | A1 | | 9/2008 | Kim et al. | |

FOREIGN PATENT DOCUMENTS

| EP | 1 498 746 A1 | 1/2005 |
|---|---|---|
| JP | 2004-166897 A | 6/2004 |
| JP | 2008-515520 A | 5/2008 |
| KR | 10-2006-0080346 A | 7/2006 |
| KR | 10-2008-0084442 A | 9/2008 |
| WO | WO 2006/038188 A2 | 4/2006 |

OTHER PUBLICATIONS

Korean Office Action issued in Korean Patent Application No. KR 10-2010-0031847 dated Jul. 12, 2011.
Extended European Search Report issued issued in European Application No. 10157867.2 mailed Oct. 25, 2012.

* cited by examiner

*Primary Examiner* — Jacqueline Cheng
(74) *Attorney, Agent, or Firm* — McDermott Will & Emery LLP

(57) ABSTRACT

There are disclosed embodiments for an ultrasound system for providing a color M mode image and a brightness M mode image. A control unit calculates a time period expected to perform a first operation for the color M mode image and a second operation for the brightness M mode image once respectively, and determines an acquisition pattern defining an order of performing the first and second operations based on the calculated time period, a sweep period, and an ensemble number. The control unit controls the acquisition unit to perform, within the sweep period, the first operation a number of times equal to the ensemble number and the second operation one or more times according to the acquisition pattern. An image processor forms the color M mode image based on the first ultrasound data and forms the brightness M mode image based on the second ultrasound data.

8 Claims, 7 Drawing Sheets

FIG. 7

| ORDER | FIRST ULTRASOUND DATA | SECOND ULTRASOUND DATA | |
|---|---|---|---|
| 1 | $CM_1$ | $BM_1$ | |
| 2 | $CM_2$ | $BM_2$ | |
| 3 | $CM_3$ | $BM_3$ | |
| 4 | $CM_4$ | $BM_4$ | |
| 5 | $CM_5$ | $BM_5$ | |
| 6 | $CM_6$ | $BM_6$ | |
| 7 | $CM_7$ | $BM_7$ | |
| 8 | $CM_8$ | $BM_8$ | |
| 9 | $CM_9$ | $BM_9$ | |
| 10 | $CM_{10}$ | $BM_{10}$ | |
| 11 | $CM_{11}$ | $BM_{11}$ | |
| 12 | $CM_{12}$ | $BM_{12}$ | |
| 13 | $CM_{13}$ | $BM_{13}$ | |
| 14 | $CM_{14}$ | $BM_{14}$ | |
| 15 | $CM_{15}$ | $BM_{15}$ | |
| 16 | $CM_{16}$ | $BM_{16}$ | |
| 17 | $CM_{17}$ | $BM_{17}$ | |
| 18 | $CM_{18}$ | $BM_{18}$ | ← SP |
| 19 | $CM_{19}$ | $BM_{19}$ | |
| ⋮ | ⋮ | ⋮ | |

FIG. 8

| ORDER | FIRST ULTRASOUND DATA | SECOND ULTRASOUND DATA | |
|---|---|---|---|
| 1 | $CM_1$ | | |
| 2 | $CM_2$ | | |
| 3 | $CM_3$ | | |
| 4 | $CM_4$ | | |
| 5 | $CM_5$ | | |
| 6 | $CM_6$ | | |
| 7 | $CM_7$ | | |
| 8 | $CM_8$ | | |
| 9 | | $BM_1$ | ← SP |
| 10 | $CM_9$ | | |
| 11 | $CM_{10}$ | | |
| 12 | $CM_{11}$ | | |
| 13 | $CM_{12}$ | | |
| 14 | $CM_{13}$ | | |
| 15 | $CM_{14}$ | | |
| 16 | $CM_{15}$ | | |
| 17 | $CM_{16}$ | | |
| 18 | | $BM_2$ | ← SP |
| 19 | $CM_{17}$ | | |
| ⋮ | ⋮ | ⋮ | |

ULTRASOUND SYSTEM AND METHOD OF PROVIDING COLOR M MODE IMAGE AND BRIGHTNESS M MODE IMAGE

The present application claims priority from Korean Patent Application No. 10-2009-29678 filed on Apr. 7, 2009, the entire subject matter of which is incorporated herein by reference.

TECHNICAL FIELD

The present disclosure relates to ultrasound systems, and more particularly to an ultrasound system and a method of providing a color M mode image and a brightness M mode image corresponding to an M line set on a color Doppler mode image and a B mode (brightness mode) image.

BACKGROUND

An ultrasound system has been extensively used for acquiring internal information of a target object due to its non-invasive and non-destructive nature. Since the ultrasound system may provide a high resolution image in real-time without any surgical treatment, it has proven to be very helpful in the medical profession.

Generally, the ultrasound system provides B mode (brightness mode) that shows a reflection coefficient of a ultrasound signal reflected from a target object in a 2-dimensional image, doppler mode showing an image of a moving target object using doppler effect, motion mode (M mode) showing a change of biometric information (e.g., brightness information) over time of a target object in a particular part of a B mode image, and elastic mode showing a difference of reaction between a target object with and without compression in an image.

Also, the ultrasound system sets an M line on the B mode image and the color doppler mode image, and provides the color M mode image and the brightness M mode image corresponding to the M line. The color M mode image may show how the blood flow changes over time on the M line. Typically, the M mode acquires ultrasound data within a particular time interval (i.e., sweep period) and displays an M mode image formed from the acquired ultrasound data. The sweep speed of the color M mode is commonly used in a range of 60 to 360 Hz, which is not sufficient from the point of the time resolution. In the brightness M mode, assuming that the velocity of sound is 1540 m/s and the depth is 15 cm, the time required to acquire the ultrasound data corresponding to one scan line is very short, i.e., approximately 200 µs, when the pulse repetition frequency (PRF) of the ultrasound is 5 KHz. Thus, the problem of the time resolution does not occur. In other words, the brightness M mode has no problem in acquiring the ultrasound data corresponding to one scan line. The color M mode acquires a plurality of ultrasound data on one scan line by repeatedly transmitting and receiving an ultrasound signal as many times as an average number of the data acquisition (an ensemble number) in the same direction. An ultrasound data acquisition period for acquiring ultrasound data of color M mode is inversely proportional to the sweep speed. For example, if the ultrasound data acquisition frequency (the PRF for radiating the ultrasound) is 2 kHz and the average number of the data acquisition is 12, then the time for forming the color M mode image according to one scan line is 6000 µs=500 µs (the ultrasound data acquisition frequency (2 kHz))×12 (the average number). In such a case, the sweep speed should be less than 160 Hz (1/6000 µs). With this low speed, it is difficult to provide continuous color M mode.

Also, as the average number is reduced to increase the sweep speed, the ultrasound data for forming the color M mode image should be reduced. This also degrades the quality of the color M mode image.

SUMMARY

Embodiments of an ultrasound system and a method adapted to provide a color M mode image and a brightness M mode image with high quality based on an average number (an ensemble number) and a sweep period for acquiring the color M mode image are disclosed herein. In one embodiment, by way of non-limiting example, the ultrasound system, comprises: an ultrasound data acquisition unit configured to perform a first operation for providing a first piece of ultrasound data for a color M mode image and a second operation for providing a second piece of ultrasound data for a brightness M mode image; a control unit configured to control the ultrasound data acquisition unit to perform the first operation by an average number of times and the second operation one or more times in a selective pattern within a predetermined sweep period to respectively accumulate the first pieces of ultrasound data and the second pieces of ultrasound data provided from the ultrasound data acquisition unit; and an image processor configured to form the color M mode image based on the accumulated first pieces of ultrasound data and to form the brightness M mode image based on the accumulated second pieces of ultrasound data.

In another embodiment, a method of providing a color M mode image and a brightness M mode image comprises: a) calculating a time period that is expected to perform first and second operations once respectively at an ultrasound data acquisition unit, a first piece of ultrasound data relating to the color M mode image being provided by the first operation and a second piece of ultrasound data relating to the brightness M mode image being provided by the second operation; b) determining an acquisition pattern defining an order of performing the first and second operations based on the calculated time period, a sweep period and an average number; c) performing the first operation by the average number of times and the second operation one or more times according to the acquisition pattern within the sweep period at the ultrasound data acquisition unit; d) forming the color M mode image based on the first pieces of ultrasound data; and e) forming the brightness M mode image based on the second pieces of ultrasound data.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

BRIEF DESCRIPTION OF THE DRAWINGS

FIGS. 7 and 8 show an example of the first pieces of ultrasound data and the second pieces of ultrasound data stored in a storage unit.

DETAILED DESCRIPTION

A detailed description may be provided with reference to the accompanying drawings.

Figure 1:
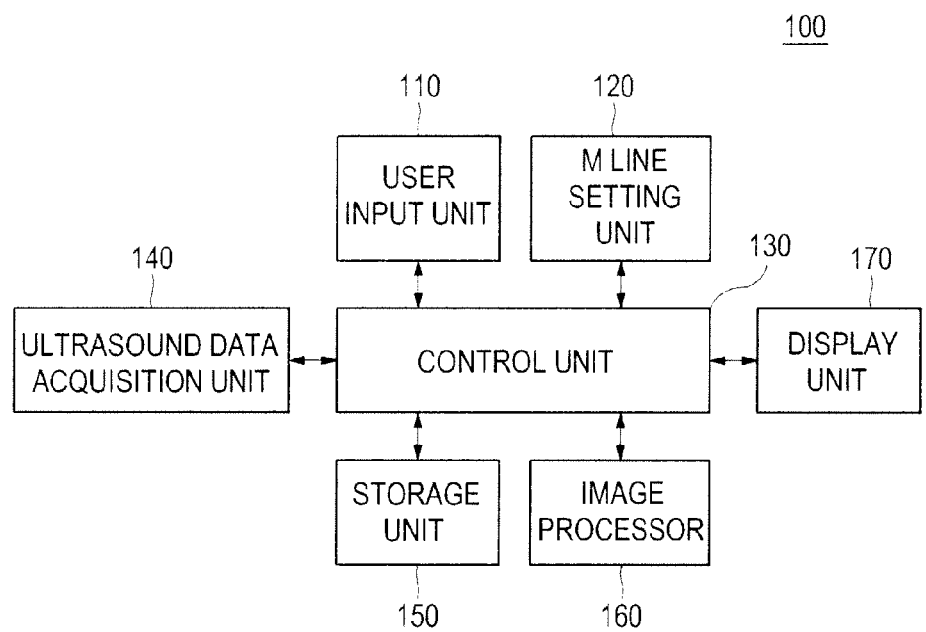
FIG. 1 is a block diagram showing an illustrative embodiment of an ultrasound system.

FIG. 1 is a block diagram showing an illustrative embodiment of an ultrasound system 100. The ultrasound system 100 comprises a user input unit 110, an M line setting unit 120, a control unit 130, an ultrasound data acquisition unit 140, a storage unit 150, an image processor 160 and a display unit 170.

Figure 4:
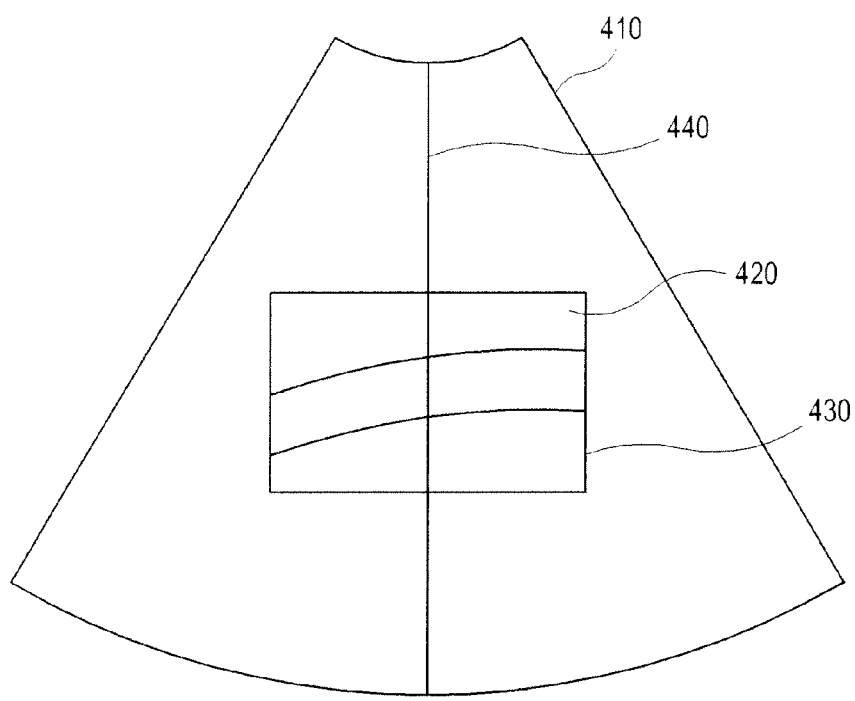
FIG. 4 shows an example of an M line set on a B mode image and color doppler mode image.

The user input unit 110 may be implemented as a control panel, a mouse, a keyboard, etc., to allow a user to input M line setting information. The M line setting information may comprise location information of the M line 440 set on a B mode (brightness mode) image 410 and a color doppler mode image 420, as illustrated in FIG. 4. The reference number 430 represents an area of interest for acquiring the color doppler mode image 420 in FIG. 4.

The M line setting unit 120 may be configured to set the M line 440 on the B mode (brightness mode) image 410 and the color doppler mode image 420 according to the M line setting information provided by the user input unit 110, as illustrated in FIG. 4. Although in the aforementioned embodiment, the M line setting unit 120 has been explained as setting the M line on the B mode image and the color doppler mode image according to the M line setting information provided by the user input unit 110, the present invention is certainly not limited thereto. In another embodiment, the M line setting unit 120 may be configured to set the M line on the B mode image and the color doppler mode image according to a predetermined M line setting information.

Figure 5:
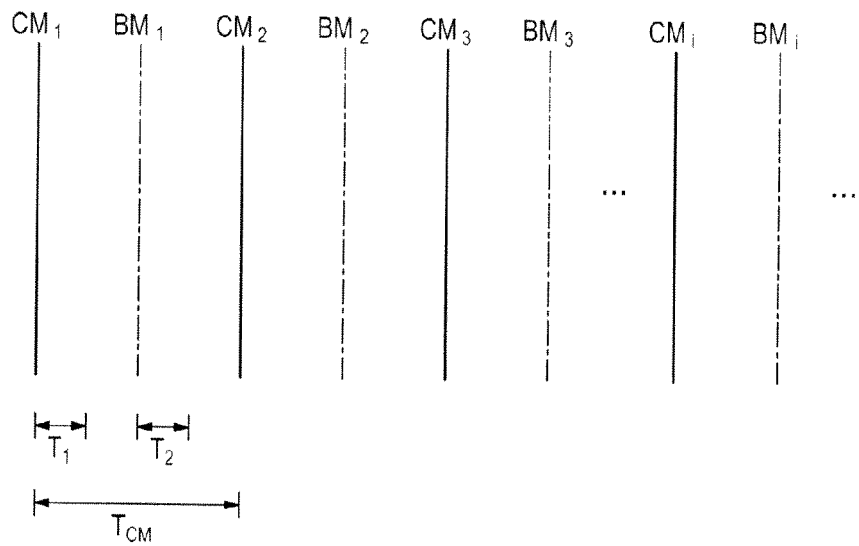
FIG. 5 and FIG. 6 show an example of acquiring first pieces of ultrasound data and second pieces of ultrasound data.
Figure 6:
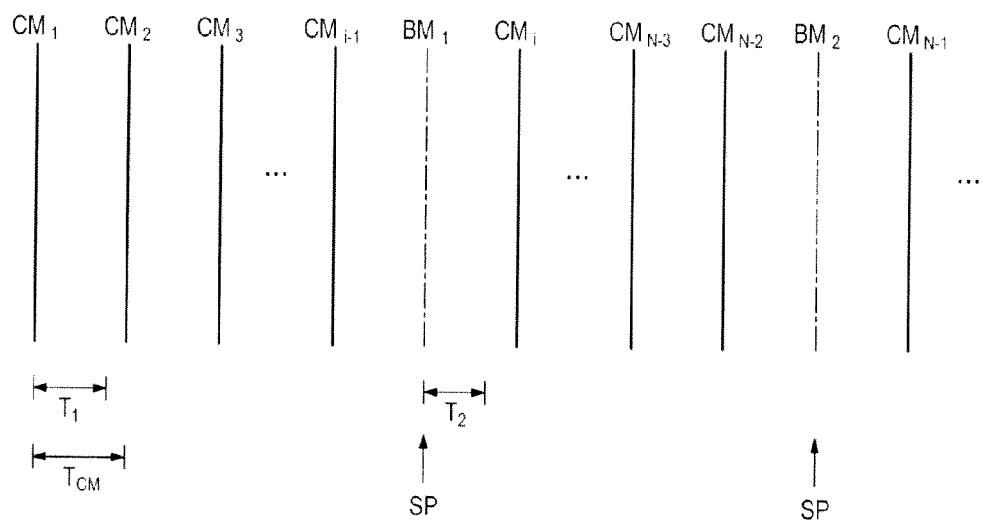

The control unit 130 may be operable to control acquisition of an ultrasound data according to a sweep speed, a sweep period, an average number, an ultrasound data acquisition period and an ultrasound data acquisition time. The sweep period is a time period of displaying an ultrasound image and the sweep speed is the end point of every sweep period. The ultrasound data acquisition period is a time period of providing a first piece of ultrasound data. In one embodiment, the ultrasound data acquisition period is equal to the sweep period divided by the average number. In one embodiment, the first piece of ultrasound data may include ultrasound data for acquiring a color motion mode (CM mode) image corresponding to the M line. The ultrasound data acquisition time includes a time period expected for providing the first piece of ultrasound data (hereinafter referred to as first time) and a time period expected for providing a second piece of ultrasound data (hereinafter referred to as second time). In one embodiment, the second piece of ultrasound data may include ultrasound data for acquiring a brightness M mode (BM mode) image corresponding to the M line. In one embodiment, the control unit 130 may calculate an aggregate time $(T_1+T_2)$ by adding the first time $(T_1)$ to the second time $(T_2)$, as illustrated in FIG. 5 and FIG. 6. The control unit 130 may compare the aggregate time $(T_1+T_2)$ with the ultrasound data acquisition period $(T_{CM})$. If the aggregate time $(T_1+T_2)$ is less than the ultrasound data acquisition period $(T_{CM})$, then the control unit 130 may control the first piece of ultrasound data (CM) and the second piece of ultrasound data (BM) to be provided alternately, as illustrated in FIG. 5. If the aggregate time $(T_1+T_2)$ is equal to or greater than the ultrasound data acquisition period $(T_{CM})$, then the control unit 130 may control the first pieces of ultrasound data (CM) to be provided by the average number and then the second piece of ultrasound data (BM) to be provided once at the sweep speed (SP), as illustrated in FIG. 6.

Further, the control unit 130 may operate to control the setting of the M line and storage of the ultrasound data. Additionally, the control unit 130 may operate to control formation and display of the CM mode image and the BM mode image according to the ultrasound acquisition period and the ultrasound acquisition time.

The ultrasound acquisition unit 140 may be operable to transmit an ultrasound signal to a target object, receive the ultrasound signal reflected from the target object (i.e., ultrasound echo signal), and provide the ultrasound data according to the control unit 130.

Figure 2:
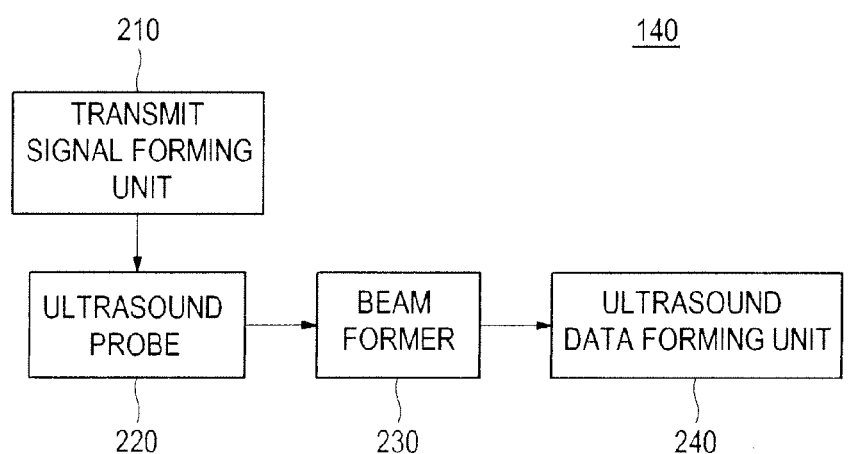
FIG. 2 is a block diagram showing an illustrative embodiment of an ultrasound data acquisition unit.

FIG. 2 is a block diagram showing an illustrative embodiment of the ultrasound data acquisition unit 140. The ultrasound data acquisition unit 140 may include a transmit signal forming unit 210, a ultrasound probe 220 including a plurality of transducer elements, a beam former 230 and a ultrasound data forming unit 240.

The transmit signal forming unit 210 may be operable to form a transmit signal to be applied to each of the transducer elements of the ultrasound probe 220. By way of a non-limiting example, the positions and focusing points of the transducer elements may be considered in forming the transmit signal. In one embodiment, the transmit signal may include a first transmit signal for acquiring the CM mode image and a second transmit signal for acquiring the BM mode image.

The ultrasound probe 220 may operate to convert the transmit signal provided by the transmit signal forming unit 210 into an ultrasound signal and transmit it to the target object. The ultrasound probe 220 may further operate to receive the ultrasound echo signal reflected from the target object and form a receive signal. In one embodiment, when the first transmit signal is provided by the transmit signal forming unit 210, the ultrasound probe 220 may operate to convert the first transmit signal into an ultrasound signal, transmit it to the target object, receive the ultrasound echo signal reflected from the target object and form a first receive signal. In one embodiment, when the second transmit signal is provided by the transmit signal forming unit 210, the ultrasound probe 220 may operate to convert the second transmit signal into an ultrasound signal, transmit it to the target object, receive the ultrasound echo signal reflected from the target object and form a second receive signal.

In one embodiment, the beam former 230 may be configured to form a first digital signal through analog-to-digital conversion of the first receive signal when the first receive signal is provided by the ultrasound probe 220. The beam former 230 may perform receive-focusing upon the first digital signal in consideration of the positions and focusing points of the transducer elements of the ultrasound probe 220, and form a first receive-focused signal thereby. In one embodiment, the beam former 230 may form a second digital signal through analog-to-digital conversion of the second receive signal when the second receive signal is provided by the ultrasound probe 220. The beam former 230 may perform receive-focusing upon the second digital signal in consideration of the positions and focusing points of the transducer elements of the ultrasound probe 220, and form a second receive-focused signal thereby.

In one embodiment, the ultrasound data forming unit 240 may be configured to form the first piece of ultrasound data using the first receive-focused signal when the first receive-focused signal is provided by the beam former 230. In one embodiment, the ultrasound data forming unit 240 may be configured to form the second piece of ultrasound data using the second receive-focused signal when the second receive-focused signal is provided by the beam former 230. Further, the ultrasound data forming unit 240 may perform various signal processing (e.g., gain adjustment, filtering) to the first and second receive-focused signal for forming the ultrasound data.

Referring back to FIG. 1, the storage unit 150 may be configured to store the first and second pieces of ultrasound data provided by the ultrasound data acquisition unit 140 according to the control unit 130. In one embodiment, the storage unit 150 may be configured to store the first pieces of ultrasound data (CM) and the second pieces of ultrasound data (BM) in the order of being provided from the ultrasound data acquisition unit 140 according to the control unit 130, as illustrated in FIG. 7. In another embodiment, the storage unit 150 may be configured to store the first pieces of ultrasound data (CM) and the second pieces of ultrasound data (BM) in the order of being provided from the ultrasound data acquisition unit 140 according to the control unit 130, as illustrated in FIG. 8.

Although in the aforementioned embodiment, the storage unit 150 has been explained as storing the first pieces of ultrasound data and the second pieces of ultrasound data, the present invention is certainly not limited thereto. In another embodiment, the storage unit 150 may include a first storage unit (not shown) for storing the first pieces of ultrasound data and a second storage unit (not shown) for storing the second pieces of ultrasound data.

The image processor 160 may be operable to extract the first pieces of ultrasound data and the second pieces of ultrasound data in consideration of the sweep speed, the average number, the ultrasound data acquisition period and the ultrasound data acquisition time according to the control unit 130. The image processor 160 may further operate to form the CM mode image and the BM mode image based on the extracted first and second pieces of ultrasound data.

Figure 3:
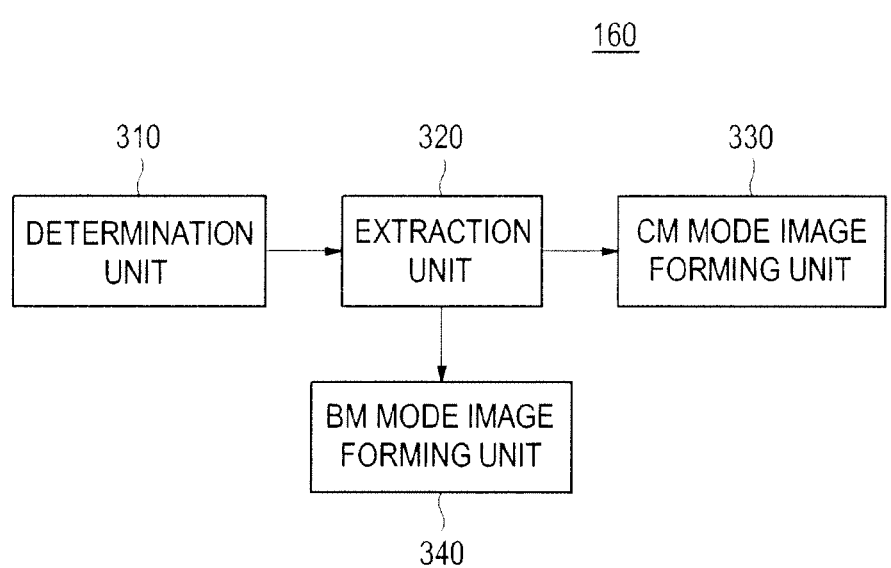
FIG. 3 is a block diagram showing an illustrative embodiment of an image processor.

FIG. 3 is a block diagram showing an illustrative embodiment of the image processor 160. The image processor 160 may include a determination unit 310, an extraction unit 320, a CM mode image forming unit 330 and a BM mode image forming unit 340.

The determination unit 310 may be configured to form a determination result using the sweep speed, the average number, the ultrasound data acquisition period and the ultrasound data acquisition time. In one embodiment, the determination unit 310 may be configured to form first determination information if the ultrasound data acquisition time, which is the aggregate time $(T_1+T_2)$ calculated by adding the first time to the second time, is less than the ultrasound data acquisition period $(T_{CM})$, as illustrated in FIG. 5. In one embodiment, the determination unit 310 may be configured to form second determination information if the aggregate time $(T_1+T_2)$ calculated by adding the first time to the second time is equal to or more than the ultrasound data acquisition period $(T_{CM})$, as illustrated in FIG. 6.

The extraction unit 320 may be configured to extract the first pieces of ultrasound data and the second pieces of ultrasound data based on the sweep speed when the first determination information is provided by the determination unit 310. In one embodiment, the extraction unit 320 may be configured to extract a predetermined number (e.g., 12) of the first pieces of ultrasound data ($CM_{18}$-$CM_7$) starting at the first piece of ultrasound data ($CM_{18}$), which is lastly stored during the sweep period, from the storage unit 150, as illustrated in FIG. 7. The extraction unit 320 may further operate to extract the second piece of ultrasound data ($BM_{18}$), which is lastly stored during the sweep period, from the storage unit 150. In another embodiment, the extraction unit 320 may be configured to extract a predetermined number (e.g., 12) of the first pieces of ultrasound data ($CM_{18}$-$CM_7$) starting at the first piece of ultrasound data ($CM_{18}$), which is lastly stored during the sweep period, from the storage unit 150, as illustrated in FIG. 7. The extraction unit 320 may further operate to extract a predetermined number (e.g., 12) of the second pieces of ultrasound data ($BM_{18}$-$BM_7$) starting at the second piece of ultrasound data ($BM_{18}$), which is lastly stored during the sweep period, from the storage unit 150, as illustrated in FIG. 7.

The extraction unit 320 may be configured to extract a predetermined number of the first pieces of ultrasound data and the second pieces of ultrasound data accumulated during the sweep period from the storage unit 150 when the second determination information is provided by the determination unit 310. In one embodiment, the extraction unit 320 may be configured to extract a predetermined number (e.g., 12) of the ultrasound data (i.e., ten of the first pieces of ultrasound data ($CM_{16}$-$CM_7$) and two of the second pieces of ultrasound data ($BM_2$, $BM_1$) starting at the second piece of ultrasound data ($BM_2$), which is lastly stored during the sweep period, from the storage unit 150, as illustrated in FIG. 8.

The CM mode image forming unit 330 may operate to form the CM mode image based on the first pieces of ultrasound data extracted by the extraction unit 320. In one embodiment, when the first pieces of ultrasound data ($CM_{18}$-$CM_7$) extracted by the extraction unit 320 are provided, the CM mode image forming unit 330 may operate to calculate mean power, mean velocity and variance corresponding to the CM mode image based on the first pieces of ultrasound data ($CM_{18}$-$CM_7$) and form the CM mode image using the calculated mean power (P), mean velocity (v) and variance ($\sigma^2$). By way of a non-limiting example, mean power, mean velocity and variance may be calculated according to the following equation (1).

$$P = R[0] = \frac{1}{N}\left(\sum_{n=0}^{n=N-1} x[n]x[n]^*\right) \quad (1)$$

$$R[1] = \frac{1}{N-1}\sum_{n=0}^{N-2} x[n]^* x[n+1]$$

$$v = \tan^{-1}(\mathrm{Im}(R[1])/\mathrm{Re}(R[1]))/\pi$$

$$\sigma^2 = 1 - \frac{|R[1]|}{R[0]}$$

In equation 1, R[0] denotes $0^{th}$ order autocorrelation, R[1] denotes $1^{th}$ order autocorrelation, "N" denotes the average number, x[n] denotes the input signal (e.g., $CM_{18}$-$CM_7$), x[n]* denotes the complex conjugate number of the input signal, Im( ) denotes an imaginary part of a complex number, and Re( ) denotes a real part of the complex number.

In another embodiment, when the first pieces of ultrasound data ($CM_{16}$-$CM_7$) extracted by the extraction unit 320 are provided, the CM mode image forming unit 330 may operate to calculate mean power, mean velocity and variance corresponding to the CM mode image using the first pieces of ultrasound data ($CM_{16}$-$CM_7$), and form the CM mode image using the calculated mean power, mean velocity and variance.

By way of a non-limiting example, mean power (P), mean velocity (v) and variance ($\sigma^2$) may be calculated according to the following equation (2).

$$P = R[0] = \frac{1}{N-K}\left(\sum_{n=0}^{M-1} x[n]x[n]^* + \sum_{n=M+K}^{N-1} x[n]x[n]^*\right) \quad (2)$$

$$v = \tan^{-1}(\mathrm{Im}(R[1])/\mathrm{Re}(R[1]))/\pi$$

$$R[1] = \frac{1}{N-K-1}\left(\sum_{n=0}^{M-1} x[n]^* x[n+1] + \sum_{n=M+K}^{N-2} x[n]^* x[n+1]\right)$$

$$\sigma^2 = 1 - \frac{|R[1]|}{R[0]}$$

In equation 2, "M" denotes the order in which the ultrasound data were not provided at the sweep speed, "K" denotes the number of the ultrasound data which were not provided at the sweep speed.

Figure 9:
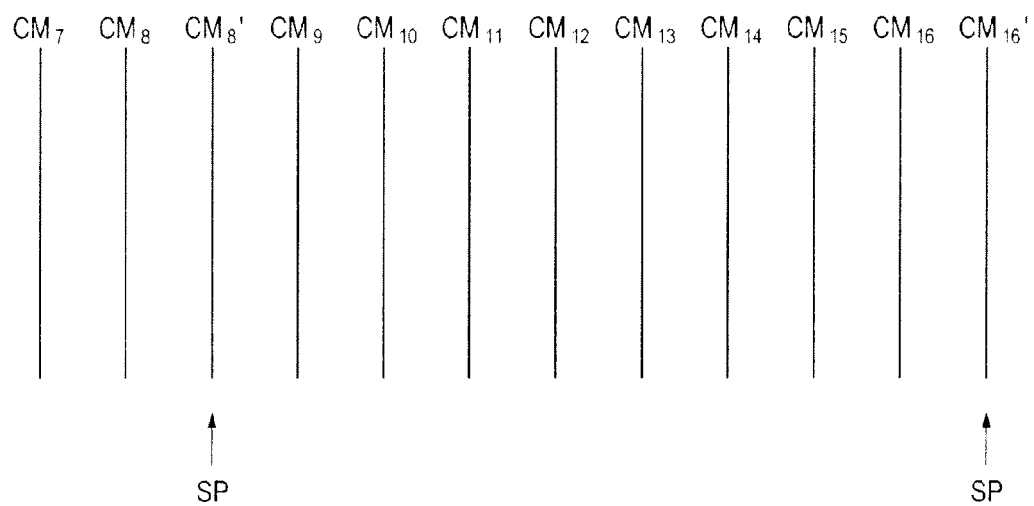
FIG. 9 shows an example of third pieces of ultrasound data obtained through interpolation of the first pieces of ultrasound data.

In yet another embodiment, when the first pieces of ultrasound data ($CM_{16}$-$CM_7$) extracted by the extraction unit 320 are provided, the CM mode image forming unit 330 may operate to obtain third pieces of ultrasound data ($CM_8'$ and $CM_{16}'$), which were not provided at the sweep speed, with the use of interpolation of the first pieces of ultrasound data ($CM_{16}$-$CM_7$) as illustrated in FIG. 9. The CM mode image forming unit 330 may further operate to calculate an error comparing the first pieces of ultrasound data ($CM_{16}$-$CM_7$) extracted by the extraction unit 320 with the third pieces of ultrasound data ($CM_8'$ and $CM_{16}'$) obtained by using the interpolation. If the calculated error is less than a predetermined threshold, then the CM mode image forming unit 330 may operate to calculate mean power, mean velocity and variance using the first pieces of ultrasound data ($CM_{16}$-$CM_7$) extracted by the extraction unit 320 and the third pieces of ultrasound data ($CM_8'$ and $CM_{16}'$) obtained by using the interpolation, and form the CM mode image using the calculated mean power, mean velocity and variance. Assuming that the number of third pieces of ultrasound data obtained by using the interpolation is K, the third pieces of ultrasound data obtained by using the interpolation are located at M, M+1, and the total number of the first and third pieces of ultrasound data is N. Under the above conditions, mean power ($P_{total}$), mean velocity ($v_{total}$) and variance ($\sigma^2_{total}$) may be calculated according to the following equation (3).

$$P_{total} = R[0]_{total} = \quad (3)$$

$$\frac{1}{N-K}\left(\sum_{n=0}^{M-1} x[n]x[n]^* + \sum_{n=M+K}^{N-1} x[n]x[n]^*\right) + \frac{1}{K}\left(\sum_{n=M}^{M+1} x[n]x[n]^*\right)$$

$$R[1]_{total} = \frac{1}{N-K-1}\left(\sum_{n=0}^{M-1} x[n]^* x[n+1] + \sum_{n=M+K}^{N-2} x[n]^* x[n+1]\right) + \frac{1}{K}\sum_{n=M-1}^{M+K} x[n]^* x[n+1]$$

$$v_{total} = \frac{\tan^{-1}(\mathrm{Im}(R[1]_{total})/\mathrm{Re}(R[1]_{total}))}{\pi}$$

$$\sigma^2_{total} = 1 - \frac{|R[1]_{total}|}{R[0]_{total}}$$

$$P_{IP} = R[0]_{IP} = \frac{1}{K}\left(\sum_{n=M}^{M+1} x[n]x[n]^*\right)$$

$$R[1]_{IP} = \frac{1}{K}\sum_{n=M-1}^{N+K} x[n]^* x[n+1]$$

$$v_{IP} = \frac{\tan^{-1}(\mathrm{Im}(R[1]_{IP})/\mathrm{Re}(R[1]_{IP}))}{\pi}$$

$$\sigma^2_{IP} = 1 - \frac{|R[1]_{IP}|}{R[0]_{IP}}$$

In equation (3), $P_{IP}$, $v_{IP}$ and $\sigma^2_{IP}$ respectively represent mean power, mean velocity and variance, which are calculated from the third pieces of ultrasound data ($CM_8'$ and $CM_{16}'$) obtained by using the interpolation, $R[0]_{IP}$ denotes $0^{th}$ order autocorrelation, which is calculated from the third pieces of ultrasound data ($CM_8'$ and $CM_{16}'$), $RP[1]_{IP}$ denotes $1^{th}$ order autocorrelation, which is calculated from the third pieces of ultrasound data ($CM_8'$ and $CM_{16}'$).

If the calculated error is more than the predetermined threshold, then the CM mode image forming unit 330 may operate to calculate mean power, mean velocity and variance only using the first pieces of ultrasound data ($CM_{16}$-$CM_7$) extracted by the extraction unit 320, and form the CM mode image using the calculated mean power, mean velocity and variance.

The BM mode image forming unit 340 may operate to form a BM mode image based on the second pieces of ultrasound data extracted by the extraction unit 320. In one embodiment, when the second piece of ultrasound data ($BM_{18}$) extracted by the extraction unit 320 is provided, the BM mode image forming unit 340 may operate to form the BM mode image based on the second piece of ultrasound data ($BM_{18}$). In another embodiment, when the second pieces of ultrasound data ($BM_{18}$-$BM_7$) extracted by the extraction unit 320 are provided, the BM mode image forming unit 340 may operate to form the BM mode image through performing, for example, line average to the second pieces of ultrasound data ($BM_{18}$-$BM_7$). In yet another embodiment, when the second pieces of ultrasound data ($BM_1$ and $BM_2$) extracted by the extraction unit 320 are provided, the BM mode image forming unit 340 may operate to form the BM mode image through performing, for example, line average to the second pieces of ultrasound data ($BM_1$ and $BM_2$).

Referring back to FIG. 1, the display unit 170 may operate to display the CM mode image and the BM mode image formed at the image processor 160 according to the control unit 130. The display unit may further operate to display the B mode image 410, the color doppler mode image 420 and the M line 440, as illustrated in FIG. 4. In one embodiment, the display unit 170 may include a liquid crystal display (LCD), a cathode ray tube (CRT) or any other device capable of displaying an image.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements within the scope of the disclosure, the drawings and the appended claims. In addition to variations and modifications in the component parts and/or arrangements, alternative uses will also be apparent to those skilled in the art.

What is claimed is:

1. An ultrasound system, comprising:
an ultrasound data acquisition unit configured to perform a first operation for providing first ultrasound data for forming a color M mode image and a second operation for providing second ultrasound data for forming a brightness M mode image;

a control unit configured to calculate a time period expected to perform the first and second operations once respectively and to determine an acquisition pattern defining an order of performing the first and second operations based on the calculated time period, a sweep period and an ensemble number, the control unit being further configured to control the ultrasound data acquisition unit to perform, within the sweep period, the first operation a number of times equal to the ensemble number and the second operation one or more times according to the acquisition pattern; and an image processor configured to form the color M mode image based on the first ultrasound data and to form the brightness M mode image based on the second ultrasound data.

2. The ultrasound system of claim 1, wherein the acquisition pattern is a pattern in which the first operation and the second operation alternate, when a time period expected for the ultrasound data acquisition unit to perform the first and second operations once respectively is less than the sweep period divided by the ensemble number.

3. The ultrasound system of claim 1, wherein the acquisition pattern is a pattern in which the first operation is performed the number of times equal to the ensemble number and then the second operation is performed once, when a time period expected for the ultrasound data acquisition unit to perform the first and second operations once respectively is equal to or more than the sweep period divided by the ensemble number.

4. The ultrasound system of claim 3, wherein the image processor is configured to obtain third ultrasound data by using interpolation of the first ultrasound data provided by the ultrasound data acquisition unit during the sweep period and form the color M mode image based on the first ultrasound data and the third ultrasound data.

5. A method of providing a color M mode image and a brightness M mode image, comprising:

a) calculating a time period expected to perform a first operation and a second operation once respectively at an ultrasound data acquisition unit, wherein first ultrasound data relating to the color M mode image is provided by the first operation and second ultrasound data relating to the brightness M mode image is provided by the second operation;

b) determining an acquisition pattern defining an order of performing the first operation and the second operation based on the calculated time period, a sweep period and an ensemble number;

c) performing the first operation a number of times equal to the ensemble number and performing the second operation one or more times according to the acquisition pattern, within the sweep period at the ultrasound data acquisition unit;

d) forming the color M mode image based on the first ultrasound data; and e) forming the brightness M mode image based on the second ultrasound data.

6. The method of claim 5, wherein the acquisition pattern is a pattern in which the first operation and the second operation alternate, when the calculated time period is less than the sweep period divided by the ensemble number.

7. The method of claim 5, wherein the acquisition pattern is a pattern in which the first operation is performed the number of times equal to the ensemble number and then the second operation is performed once, when the calculated time period is equal to or more than the sweep period divided by the ensemble number.

8. The method of claim 7, wherein forming the color M mode image further comprises:

obtaining third ultrasound data by using interpolation of the first ultrasound data provided by the ultrasound data acquisition unit during the sweep period; and forming the color M mode image based on the first ultrasound data and the third ultrasound data.

* * * * *